(12) United States Patent
Abendroth et al.

(10) Patent No.: US 9,983,212 B2
(45) Date of Patent: May 29, 2018

(54) IN VITRO METHOD FOR THE EARLY DETECTION OF A POTENTIAL INFLAMMATION, IN PARTICULAR ASSOCIATED WITH REJECTION OF A TRANSPLANT, A NEURODEGENERATIVE DISORDER OR A DEPRESSION

(71) Applicant: Salion, GmbH, Münsing (DE)

(72) Inventors: Dietmar Abendroth, Thalfingen (DE); Manfred J Stangl, Sauerlach (DE); Michael Marzinzig, Ulm (DE)

(73) Assignee: Salion GmbH, Münsing (DE)

( * ) Notice: Subject to any disclaimer, the term of this patent is extended or adjusted under 35 U.S.C. 154(b) by 269 days.

(21) Appl. No.: 14/888,729

(22) PCT Filed: May 2, 2014

(86) PCT No.: PCT/EP2014/058965
§ 371 (c)(1),
(2) Date: Nov. 3, 2015

(87) PCT Pub. No.: WO2014/177680
PCT Pub. Date: Nov. 6, 2014

(65) Prior Publication Data
US 2016/0084843 A1 Mar. 24, 2016

(30) Foreign Application Priority Data

May 3, 2013 (EP) ..................................... 13166375

(51) Int. Cl.
*G01N 33/53* (2006.01)
*G01N 33/64* (2006.01)
*G01N 33/68* (2006.01)

(52) U.S. Cl.
CPC .......... *G01N 33/64* (2013.01); *G01N 33/6893* (2013.01); *G01N 2800/245* (2013.01); *G01N 2800/7076* (2013.01); *G01N 2800/7095* (2013.01)

(58) Field of Classification Search
None
See application file for complete search history.

(56) References Cited

U.S. PATENT DOCUMENTS

| | | | | |
|---|---|---|---|---|
| 5,736,343 A | * | 4/1998 | Landry | G01N 33/5308 435/188.5 |
| 5,871,905 A | * | 2/1999 | Thieme | G01N 33/54313 435/5 |
| 6,102,872 A | * | 8/2000 | Doneen | A61B 5/14532 422/50 |

FOREIGN PATENT DOCUMENTS

EP 2 284 540 A1 2/2011

OTHER PUBLICATIONS

Diaconu et al., Colorimetric assay of salivary nitrite content, Jurnal De Medicina Prevetiva, 9(1), pp. 74-78. (Year: 2001).*
PCT/EP2014/058965—International Search Report, dated Jul. 22, 2014.
PCT/EP2014/058965—International Written Opinion, dated Jul. 22, 2014.
PCT/EP2014/058965—International Preliminary Report on Patentability, dated Feb. 5, 2015.
Chen, et al., "Kynurenine Pathway Metabolites in Humans: Disease and Healthy States", School of Medical Sciences, Darlinghurst 2010, Australia.

* cited by examiner

Primary Examiner — Gary Counts
(74) Attorney, Agent, or Firm — Curatolo Sidoti Co., LPA; Salvatore A. Sidoti; Floyd Trillis, III

(57) ABSTRACT

An in vitro method for the early detection of a potential inflammation, in particular a rejection of a transplant is disclosed, wherein the level of kynurenine in saliva is determined. The test method can be easily performed and allows the early detection of potential problems.

10 Claims, 7 Drawing Sheets

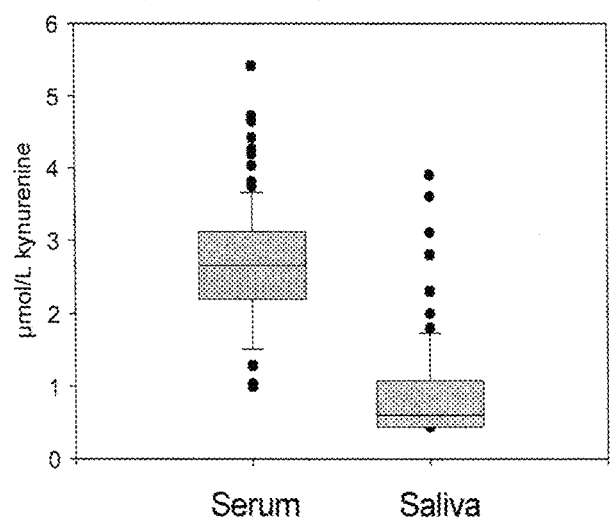
Fig.5: Comparison between serum and saliva kynurenine-levels. Serum results are nearly 4 times higher in normal controls.

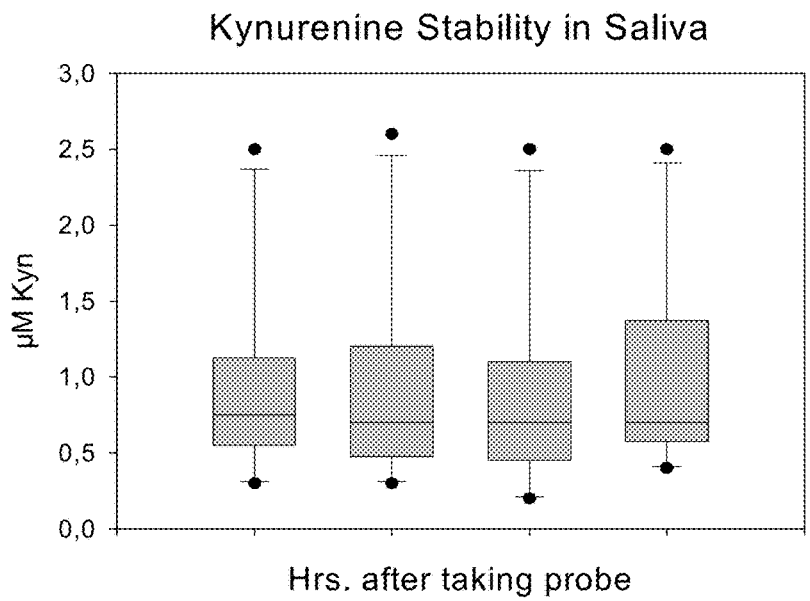

Fig.6:
Stability of kynurenine after taking the probe. No in-/decrease of the metabolite over a period of 4 hrs was found which is much more than reliable for the testing.

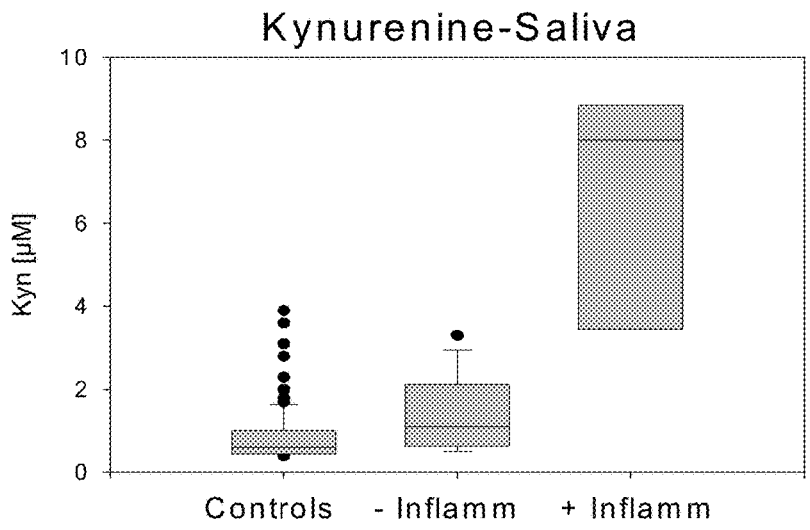

Fig.7:
Identification of inflammation in 6 patients (+Inflamm) vs. 12 patients without inflammation. There was a significant difference (p<.004). The inflammatory response was detected 5 days (median) before any clinical syndrome occurred.

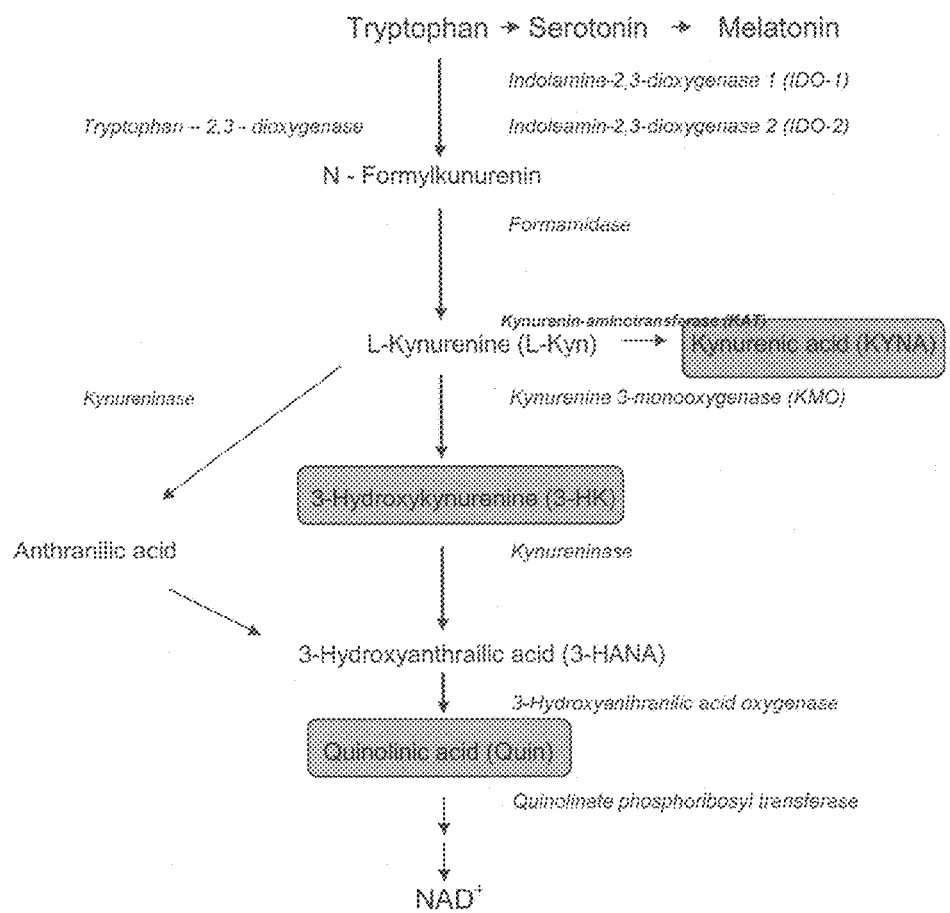
Fig. 8: Schematic overview of the kynurenine pathway, the major route of tryptophan degradation in higher eukaryotes. Enzymes are indicated in italics. The neurotoxic metabolites Quin and 3-HK are highlighted in red and the neuroprotective metabolite KYNA in green

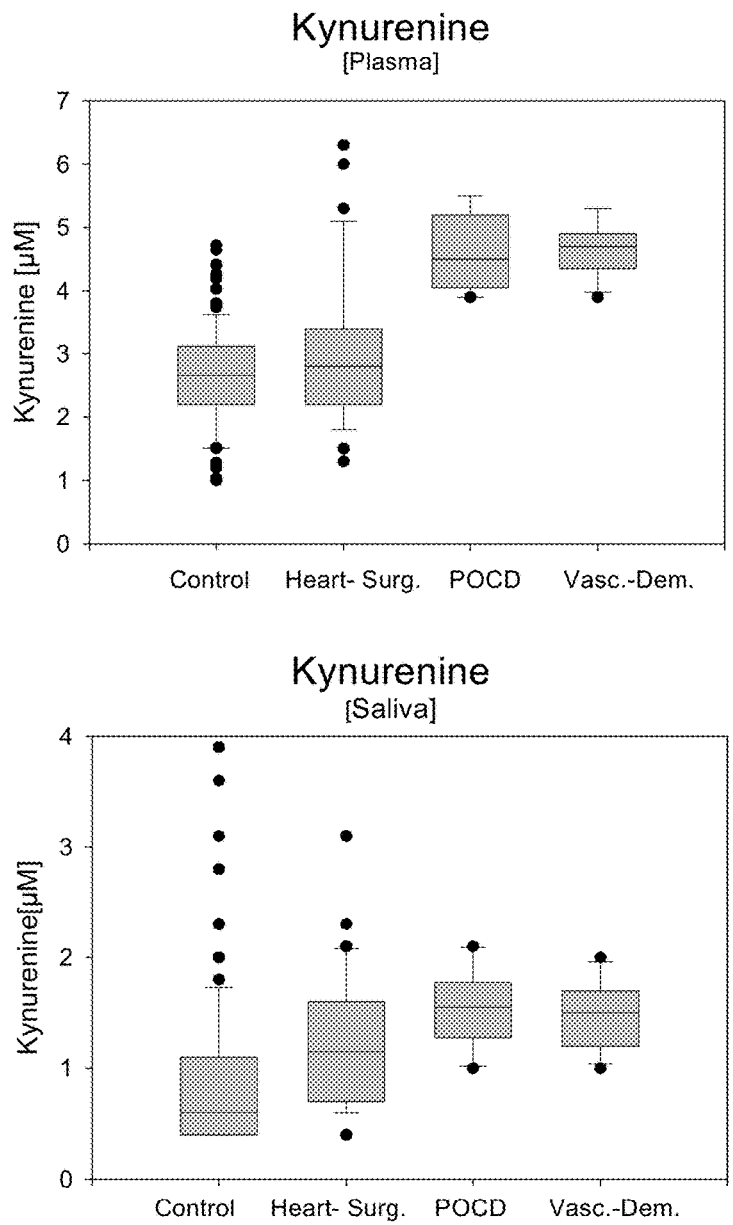

Fig. 9: Comparison of Kynurenin (measured in plasma and in saliva) in 4 groups: Control n=116; patients before heart surgery n= 51; patients with postoperative cerebral disorder n=8 and patients with cerebral dementia (before therapy) n=9.

There was a significant difference between control , POCD and vascular dementia ($p<0.001$). Similar results between heart-surgery and POCD and VD ($p<0.05$), found in both plasma and saliva.

IN VITRO METHOD FOR THE EARLY DETECTION OF A POTENTIAL INFLAMMATION, IN PARTICULAR ASSOCIATED WITH REJECTION OF A TRANSPLANT, A NEURODEGENERATIVE DISORDER OR A DEPRESSION

CROSS REFERENCE TO RELATED APPLICATIONS

This application is a national stage application under 35 U.S.C. 371 of International Application No. PCT/EP2014/058965, filed 2 May 2014, which claims priority from European Patent Application No. 13166375.9, filed 3 May 2013, from which applications priority is claimed, and which are both incorporated herein by reference.

TECHNICAL FIELD

The present invention relates to the field of diagnosis. Modern medical treatments affect more and more people since medicine achieved substantial progress in the treatment of diseases, in particular by replacing parts of the body or organs by substitution with parts derived from foreign sources. When parts of the body and in particular organs do not function properly it is possible to transplant organs or to replace parts of the body by artificial elements like for example implanted teeth. Such treatments cause frequently a response of the body which starts frequently with an inflammation and may finally result in the rejection of the transplant.

BACKGROUND

EP 2 284 540 A1 discloses a method to diagnose organ failure. This failure might be inflammation related (sepsis). The method describes the use of a quantitative metabolomics profile and compares results with a quantitative reference metabolomics profile of a certain amount of endogenous metabolites. The idea behind this seems to detect organ failure due to infection/sepsis. In the application here is nothing said about transplantation, rejection and its pattern in saliva.

The present invention, however, discloses a method to detect and diagnose early inflammation. The method describes the use of qualitative metabolomics profile and compares results with a quantitative reference. The idea behind seems to detect early inflammatory responses in sense of detection of activation of the innate immune response. This activation is unique found in several diseases especially in the beginning. It is a reaction on either pathogens or molecules called alarmins and is leading to an activation of the inflammasome. The next step is the activation of the adaptive immune response at least 6 to 7 days later.

The human body recognizes elements implanted within the body as not compatible when the implants are not derived from the same body. Therefore, the compatibility of the foreign implant and the recipient has to be carefully examined and potential rejection actions have to be carefully monitored. When solid organs like heart, liver, lung, pancreas or kidney are transplanted the rejection actions of the recipient body are usually downregulated by suitable treatment with medicaments. The undesired side effect is, however, that the downregulation of the body's response against the transplant frequently causes simultaneously a downregulation of the immune response.

Consequently a patient receiving a transplant has to be very carefully monitored with regard to a potential infection (e.g. bacterial or viral) since such an infection may be deadly to the patient having received a transplant. The complex medical treatment of a person having received a transplant has, however, the undesired side effect that a patient does not realize the early signs of an infection and/or inflammation. The rejection of a transplant may cause an inflammation whereby the early stages are normally not recognized by the patient due to the medical treatment after transplantation. The patient will realize only at a later stage that he or she suffers from an inflammation which has, however, the undesired consequence that it may be too late to start with a suitable treatment of the patient in order to avoid the rejection of the transplant. Therefore, there is a need for a simple and reliable in vitro method for the early detection of a potential inflammation, in particular the detection of a potential rejection of a transplanted organ.

SUMMARY

The present invention relates to the kynurenine pathway. Tryptophan is an essential amino acid that can be metabolized through different pathways, a major route being the kynurenine pathway. This pathway is illustrated in FIG. 1. The first enzyme of the pathway, indolamine-2,3-dioxygenase, is strongly stimulated by inflammatory molecules, particularly interferon-γ. Thus, the kynurenine pathway is often systematically up-regulated when the immune response is activated. The biological significance is that on the one hand the depletion of tryptophan and generation of kynurenines play a key modulary role in the immune response. On the other hand it was found surprisingly that the level of kynurenine measured in the saliva can be used for the early detection of a potential transplant rejection reaction which can otherwise not be easily detected.

DETAILED DESCRIPTION

The activation of indole amine 2,3-dioxygenase (IDO I), the main enzyme involved in the catabolism of tryptophan, generates immunosuppressive metabolites which counter-regulates immune activation. The interest of transplant immunologists to this control circuit rose sharply after it could be shown that IDO activity is of critical importance for immunologic acceptance of semiallogeneic foetuses in a mouse model. Experimental data led to the hypothesis that regulatory T-cells exert their immunosuppressive function by initiation of IDO activity. This basic findings made the tryptophan metabolism also of interest for clinical transplantation and different diseases (Chen et al., Int. J. of Tryptophan Research 2009; 2, 1-19).

A reliable monitoring method for the early measurement and prediction of inflammatory developments is beneficial for the therapy of the patient.

Today it is known that the endothelium, once considered to be relative inert, is involved in various functions such as fibrinolysis, coagulation, vascular tone, growth and immune response. The most common reaction in the human body might be seen in the inflammatory response mediated by the innate immunity.

Indole amine 2,3 dioxygenase (IDO), an IFN-γ-inducible intracellular enzyme, catalyzes the first and rate-limiting step in the degradation of the essential amino acid tryptophan in the kynurenine pathway. The immunmodulatory effects of IDO are represented by the prevention of T cell proliferation, promotion of T cell apoptosis, induction of T cell ignorance, anergy, and generation of T regulatory cells. While IDO emerges as a regulator of immunity, its role in controlling allo-response is unfolding.

The method disclosed herein can be used as a convenient monitoring tool, to measure inflammation or activated innate immune response. Despite growing recognition of the molecular T-cell regulatory mechanisms of IDO, its physiologic role in alloimmunity and clinical transplantation remains controversial. Available experimental data indicate that genetic manipulation by introduction of the IDO gene into allografts is associated with prolonged survival and that antigen-presenting cells (APCs), such as dendritic cells, can increase the expression of IDO and thus regulate immune responses. Furthermore, IDO acts as a bridge between dendritic cells and regulatory T cells (Tregs) to acquire full effector function. These findings show that IDO has considerable potential for immunoregulation and antigen-specific tolerance induction in transplantation. This applies equally to kynurenine. Kynurenine is the first degradation product of tryptophan after N-formyl kynurenine. Kynurenine shows the activation of an inflammatory response quite early and can be used for the early detection of a rejection episode.

The present invention provides an in vitro method for the early detection of a potential inflammation which is in particular related to the rejection of a transplant. In said method the level of kynurenine in saliva is determined. Whereas in the method of the present invention the level of L-kynurenine is preferably determined it is, however, also possible to determine the level of N-formyl kynurenine, 3-hydroxykynurenine and kynureninic acid. Depending on the method of detection it may be possible to determine between the different intermediates. It is, however, also possible to use determination tests which react with the different intermediates. The determination of kynurenine in saliva is preferably performed quantitatively or semi-quantitatively since it is important to detect changes of the level of kynurenine which are outside the regular range. It is particularly advantageous that the in vitro method can be performed without a doctor or medically trained people.

The method of the present invention is preferably used to detect as soon as possible any complication which may be related to the rejection of a transplanted organ. In preferred embodiments of the present invention the transplanted organ is selected from those organs which are frequently transplanted like kidney, liver, pancreas, heart or lung.

In another embodiment, however, the method of the present invention can be applied when parts of the body are transplanted. Such parts can be parts of the eye like cornea or retina. Also other body parts can be transplanted such as cartilage, bone, bone marrow or skin.

In a further embodiment the transplants are not derived from another human being or from an animal. In such embodiment the transplant is prepared from material which is not derived from another human or animal body. Such materials may be bone replacements, joint replacements, implants for tooth, breast implants or penis implants to mention only a few. Usually such materials are selected in order to keep potential rejection activities of the body at the lowest possible level.

It may, however, be helpful to monitor the acceptance of the transplant and a method for the early detection of a potential complication which may lead to a final rejection of the transplant. The in vitro method of the present invention can be preferably used for the easy and reliable monitoring of the recovery of a patient after having received a transplant.

In a particularly preferred embodiment of the present invention the test method described herein can be used for therapy control. It is possible to detect at a very early stage first signs of an inflammation without the requirement of invasive measures. The patient can easily perform the tests by using his saliva and the test kits provided herein allow an early indication of potential risks in therapy.

In another embodiment the present invention provides suitable kits for performing the method according to the invention. Such a kit comprises means for the determination of kynurenine in saliva. Such means may work on different principles. It is possible to use a specific color reagent which detects the presence of kynurenine and/or kynurenine derivatives. Alternatively the kit may comprise at least one or preferably two antibodies specifically binding to kynurenine. Preferably when two antibodies are used, such antibodies do not bind to the same epitope in order to allow the formation or a sandwich formed by the first antibody, kynurenine or its derivative and the second antibody.

In one embodiment of the present invention the determination of kynurenine or derivatives thereof is performed by a coloring reaction. The sample in the determination test is saliva. Before the content of kynurenine or derivatives thereof can be determined, components which may negatively affect the correct and precise test result have to be removed. In a preferred embodiment undesired components of saliva which may disturb the correct test result are removed preferably by precipitation of the components which disturb the result of the measurement. Such precipitation can preferably be performed by using trichloric acid. It is, however, possible to use other methods for deproteinization of saliva than using trichloric acid. After the disturbing components of saliva have been removed by precipitation it may be necessary to separate the phases by centrifugation. The supernatant is then preferably reacted with a coloring reagent which may preferably be Ehrlich's reagent. After development of the color the samples are measured by measuring the absorbance at a suitable wavelength. Preferably the test is performed in a quantitative or semi-quantitative manner. In the test method either a calibration curve can be used or a certain threshold value is fixed in the test kit in order to avoid false positive results.

It was found that as early as day 1 post transplantation of a solid organ, serum kynurenine was significantly elevated in patients who subsequently suffered from an acute rejection episode compared with those who had an uncomplicated course after transplant surgery. These changes in tryptophan metabolism were used for developing a novel prognostic test for acute rejection of solid organ allografts. Analyzing kynurenine content immediately after transplantation can help to define the subgroup of patients most likely to experience acute rejection with additional implications for immediate implementation of graft-saving therapy.

The method of the present invention demonstrates the correlation of inflammatory activities to inflammation, like sepsis, infections and rejection in more than 15,000 probes.

Data indicate that activated innate immunity is one of the key-factors for acute and chronic graft failure. Oxidative stress induced cytokine signalling pathways may provide a more specific target for new immunosuppressants.

In another embodiment of the present invention there is provided an in vitro method for the detection and/or monitoring of a neurodegenerative disorder, wherein the level of kynurenine in saliva or in plasma is determined. By comparing the measured values with average values obtained from non-affected individuals a diagnostic prediction can be made.

In preferred embodiments the neurodegenerative disorder is selected from the group consisting of Alzheimer's disease, vascular dementia, Parkinson's disease and postoperative cognitive dysfunction. The levels of kynurenine in plasma and/or in saliva are compared with the average level of kynurenine measured in comparable individuals who are not affected by such neurodegenerative diseases.

Chronic progressive neurodegenerative diseases, such as Alzheimer's disease (AD), Parkinson's disease (PD) and vascular dementia (VD) display an increasing prevalence in parallel with the ongoing aging of the population, and have therefore generated considerable recent research interest. Despite extensive studies on the background of neurodegenerative processes, the exact molecular basis remains still to be clarified. There is accumulating evidence that the innate immune response in the brain is mainly influenced by inflammatory processes.

Although these devastating diseases have a serious impact on the quality of life of the patients, their management is often challenging. Current therapies offer mostly only symptomatic relief and no neuroprotective therapy is available. The pathomechanisms of different neurodegenerative disorders share a number of common features. Excitotoxicity, neuroinflammation, a mitochondrial disturbance and oxidative stress have been implicated in both acute and chronic neurological disorders.

Neurodegenerative processes share some common features, which are not disease-specific. While there are still a number of details that await elucidation, there are several common mechanisms that are widely accepted; the role of mitochondrial disturbances, excitotoxicity, neuroinflammation and oxidative stress appear evident.

Glutamate excitotoxicity has been implicated in the pathomechanisms of ischemic stroke, traumatic brain injury, and various neurodegenerative disorders.

AD was earlier thought to involve a distinct pathology which can be clearly distinguished from vascular dementia (VD). However, in recent years, the role of a cerebrovascular dysfunction has been linked to the neurodegenerative process of AD, and vascular risk factors have attracted growing attention in connection with AD development and progression.

Overlaps between VD and AD have long been recognized, but in recent years a complete paradigm shift has begun, and AD has been suggested to be a primarily vascular disease. Only a small proportion of AD cases have a genetic origin; the majority is sporadic. The most important risk factor for the development of AD is advancing age, the prevalence and incidence data demonstrating an increasing tendency with rising age. Again, kynurenine plays a major role in vascular regulatory processes.

Similarly, an impaired cerebral blood flow and autoregulation capacity has been observed in animal models of AD, this impairment proving to be associated with oxidative stress. These findings link the presence of AR to oxidative stress and neuroinflammation. Today under the new view of innate immune responses it can be assumed that there is an activation of the innate inflammatory response. Another topic is that kynurenine plays a major role in vascular regulatory processes.

The role of the kynurenine pathway (KP) in AD and other neurological diseases, and its modulation as a potential therapeutic strategy will be explained in more detail below.

The kynurenine pathway (KP) is the main metabolic route of tryptophan (TRP) degradation in mammals; it is responsible for more than 95% of the TRP catabolism in the human brain. The metabolites produced in this metabolic cascade, termed kynurenines, are involved in a number of physiological processes, including neurotransmission and immune responses. The KP also involves neurotoxic and neuroprotective metabolites, and alterations in their delicate balance have been demonstrated in multiple pathological processes. The central intermediate of the KP is L-kynurenine (L-KYN), where the metabolic pathway divides into two different branches. L-KYN is transformed to either the neuroprotective kynurenic acid (KYNA) or 3-hydroxy-L-kynurenine (3-OH-KYN), which is further metabolized in a sequence of enzymatic steps to yield finally NAD. The relevant details are shown in FIG. 8.

Alterations in the KP have been demonstrated in a number of neurological disorders such as Huntington disease. Imbalances in the KP have been demonstrated not only in AD, but also in other disorders in which there is a cognitive decline, and influencing this delicate balance may be of therapeutic value.

Changes in kynurenine metabolites have additionally been suggested to correlate with the infarct volume, the mortality of stroke patients and the post-stroke cognitive impairment. In another study, serum kynurenine levels and inflammatory markers were measured in patients undergoing cardiac surgery; the results indicated an association of several kynurenine metabolite levels with the post-surgical cognitive performance.

The results show increased levels of tryptophan with decreased levels of kynurenine, anthranilic acid and 3-hydroxyanthranilic acid associated with bypass, and a later increase in kynurenic acid. Levels of neopterine and lipid peroxidation products rose after surgery in non-bypass patients whereas TNF-α and S100B levels increased after bypass. Changes of neopterine levels were greater after non-bypass surgery. Cognitive testing showed that the levels of tryptophan, kynurenine, kynurenic acid and the kynurenine/tryptophan ratio, correlated with aspects of post-surgery cognitive function, and were significant predictors of cognitive performance in tasks sensitive to frontal executive function and memory. Thus, anaesthesia and major surgery are associated with inflammatory changes (activation of the innate immune response according to generation of free radicals) and alterations in tryptophan oxidative metabolism which predict, and may play a role in, post-surgical cognitive function.

KP metabolites have also been implicated in vascular cognitive impairment. As concerns AD, a substantial amount of evidence demonstrates an altered tryptophan metabolism.

From the aspect of the peripheral kynurenine metabolism, decreased KYNA levels were measured in the serum, red blood cells and CSF of AD patients. Additionally, enhanced IDO activity was demonstrated in the serum of AD patients, as reflected by an increased KYN/TRP ratio, this elevation exhibiting inverse correlation with the rate of cognitive decline. IDO activation was also correlated with several immune markers in the blood, thereby indicating an immune activation, which lends further support to the role of neuroinflammation in the pathomechanism of AD. An increased IDO activity was also confirmed by immunohistochemistry in the hippocampus of AD patients, together with an enhanced QUIN immunoreactivity.

A particularly preferred embodiment of the present invention is the diagnosis and monitoring of postoperative cognitive dysfunction. The postoperative cognitive dysfunction (POCD) is defined as new developed cognitive functional disorder after surgical procedure. Symptoms are subtle and showing manifold pattern. Mechanisms leading to this entity are still not solved entirely. Experimental results showed immunological response of the innate immune system leading to a neuroinflammation. Activation of the inflammatory response and the TNF-α and NF-kB signal cascades are destroying the integrity of the blood-brain-barrier via excretion of different cytokines.

This enables macrophages migration into the hippocampus and allows the disabling of brain memory response. Anti-inflammatory response could inhibit this proinflammatory action and dysfunction would be prohibited.

QUIN has been shown to stimulate lipid peroxidation, production of reactive oxygen species, and mitochondrial dysfunction. Studies performed in organotypic cultures of rat corticostriatal system indicate that concentrations of QUIN even just slightly higher than physiological concentrations can cause neurodegeneration after a few weeks of exposure. Spinal neurons have been found to be especially sensitive to QUIN variations causing cell death with just nanomolar concentrations of this metabolite.

The kynurenine pathway (KP) metabolizes the essential amino acid tryptophan and generates a number of neuroactive metabolites called the kynurenines. Segregated into at least two distinct branches, often termed as the "neurotoxic" and "neuroprotective" arms of the KP, they are regulated by the two enzymes kynurenine 3-monooxygenase and kynurenine aminotransferase, respectively. Interestingly, several enzymes in the pathway are under tight control of inflammatory mediators and even small changes can cause major injuries. Recent years have seen a tremendous increase in our understanding of neuroinflammation in CNS disease. There is evidence, that neuroinflammation is linked to the innate immune system and the role of NAPLP3 inflammasomes. This could be an option of a protective therapeutic approach in these kinds of disorders.

The involvement of immune system activation in the pathophysiology of certain psychiatric disorders is well documented. Inflammatory molecules such as pro-inflammatory cytokines could enhance the activity of the indoleamine 2,3-dioxygenase (IDO) enzyme which is the first rate-limiting enzyme of the tryptophan degradation pathway, the kynurenine pathway.

Knowledge regarding kynurenine metabolites and their involvement in neuro-physiological processes has increased dramatically in recent years. In particular, endogenous KYNA appears to tightly control firing of midbrain dopamine neurons and to be involved in cognitive functions. Thus, decreased endogenous levels of rat brain KYNA have been found to reduce firing of these neurons, and mice with a targeted deletion of kynurenine aminotransferase II display low endogenous brain KYNA levels concomitant with an increased performance in cognitive tests. It is also suggested that kynurenines participate in the pathophysiology of psychiatric disorders. Thus, elevated levels of KYNA have been found in the CSF as well as in the post-mortem brain of patients with schizophrenia. The present state of art of genetic and hormonal factors regulating kynurenine pathway of tryptophan metabolism suggests that this pathway mediates both genetic and environmental mechanisms of depression. Rate-limiting enzymes of kynurenine formation, tryptophan 2,3-dioxygenase (TDO) and indoleamine 2,3-dioxygenase (IDO) are activated by stress hormones (TDO) and/or by proinflammatory cytokines (IDO). Simultaneous presence of high producer alleles of proinflammatory cytokines genes (e.g., interferon-gamma and tumor necrosis factor-alpha) determines the genetic predisposition to depression via up-regulation of IDO while impact of environmental stresses is mediated via hormonal activation of TDO. Tryptophan-kynurenine pathway represents a major meeting point of gene-environment interaction in depression and a new target for pharmacological intervention. The method disclosed herein can therefore also be used for the diagnosis of depression.

The methods of diagnosis disclosed herein should be used together with clinical parameters. The relative value of kynurenine may preferably be interpreted together with other clinical parameters. The present invention contributes substantially to the prognostic value of the diagnosis. Very often the method of the present invention can be improved by comparing the value of kynurenine measured in the patient to be diagnosed with the average value obtained from a comparable cohort of persons who do not suffer from this disease.

The kits for performing the in vitro method as disclosed herein may be based on different principles. One of the preferred principles is known as Lateral Flow Immunochromatographic Assay. Such a Lateral Flow Immunochromatographic Assay can be easily performed by the patient without the help of a doctor or other medically trained person.

Lateral flow tests also known as Lateral Flow Immunochromatographic Assays are simple devices intended to detect the presence (or absence) of a target analyte sample without the need for specialized and costly equipment, though many lab based applications exist that are supported by a reading equipment. Typically, these tests are used for medical diagnostics either for home testing, point of care testing, or laboratory use. A widely spread and well known application is the home pregnancy test.

The technology is based on a series of capillary beds, such as pieces of porous paper or sintered polymer. Each of these elements has the capacity to transport fluid (e.g., saliva) spontaneously. The first element (the sample pad) acts as a sponge and holds an excess of sample fluid. Once soaked, the fluid migrates to the second element (conjugate pad) in which the manufacturer has stored the so called conjugate, a dried format of bio-active particles (see below) in a salt-sugar matrix that contains everything to guarantee an optimized chemical reaction between the target molecule (e.g., kynurenine) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

In principle, any colored particle can be used, however, latex (blue color) or nanometer sized particles of gold (red color) are most commonly used. The gold particles are red in color due to localized surface plasmon resonance. Fluorescent or magnetic labeled particles can also be used, however these require the use of an electronic reader to assess the test result.

The sample first encounters colored particles which are labeled with antibodies raised to the target analyte. The test line will also contain antibodies to the same target, although it may bind to a different epitope on the analyte. The test line will show as a colored band in positive samples. An example of the sandwich assay is the sandwich ELISA.

While not strictly necessary, most test kits preferably incorporate a second line which contains an antibody that picks up free latex/gold in order to confirm the test has operated correctly.

In a preferred embodiment the single components of the lateral flow assay are adapted in such a manner that the presence of kynurenine is indicated only when more than a certain threshold value of kynurenine is present in the sample.

A preferred test kit consists of the following components:
1. Sample pad—an absorbent pad onto the test sample (saliva) is applied
2. Conjugate or reagent pad—this contains antibodies specific to the target (kynurenine) analyte conjugated to colored particles (usually colloidal gold particles, or latex microspheres)
3. Reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies)
4. Wick or waste reservoir—a further absorbent pad designed to draw the sample across the reaction membrane by capillary action and collect it.

The components of the strip are usually fixed to an inert backing material and may be presented in a simple dipstick format or within a plastic casing with a sample port and reaction window showing the capture and control zones.

There are two preferred embodiments of the test kits (lateral flow immunoassay) used in the method of the present invention:

a. Double Antibody Sandwich Assays

In this format the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane show a positive result. A single line in the control zone is a negative result. Double antibody sandwich assays are most suitable for larger analytes, such as bacterial pathogens and viruses, with multiple antigenic sites. For the present invention a suitable pair of antibodies must be selected which bind to different epitopes on kynurenine.

When the test methods or kits suitable for performing such method use antibodies which bind specifically to kynurenine, the term "antibody" means not only antibodies artificially produced for example by immunization of a laboratory animal like rabbit, sheep or goat. It comprises also in a preferred embodiment monoclonal antibodies produced according to the hybridoma technology. Moreover, the term "antibody" comprises also antigen-binding fragments of antibodies such as recombinantly produced antigen-binding fragments. Such constructs can be produced by phage display and technologies derived therefrom.

b. Competitive Assays

Competitive assays are primarily used for testing small molecules and differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. Competitive assays are most suitable for testing for small molecules, such as mycotoxins, unable to bind to more than one antibody simultaneously. There are a number of variations on lateral flow technology. The capture zone on the membrane may contain immobilized antigens or enzymes—depending on the target analyte—rather than antibodies. It is also possible to apply multiple capture zones to create a multiplex test.

Lateral flow immunoassays are simple to use by untrained operators and generally produce a result within 15 minutes. They are very stable and robust, have a long shelf life and do usually not require refrigeration. They are also relatively inexpensive to produce. These features make them ideal for use at the point-of-care and for testing samples in the field, as well as in the laboratory. However, their sensitivity is limited without additional concentration or culture procedures. There are quantitative tests available, but our target is a qualitative test for saliva within a certain range. Therefore, the preferred test kit is adjusted to measure kynurenine only if present above a certain concentration. Below such concentration the test kit will show a negative result.

The method of the present invention is preferably performed with saliva. Saliva is a clinically informative, biological fluid that is useful for novel approaches to prognosis, laboratory or clinical diagnosis, and monitoring and management of patients. Saliva contains multiple biomarkers and an overview of the principles of salivary gland secretion, methods of collection, and discussion of general uses can be found in a report of a meeting published in the Annals of the New York Academy of Sciences Malamud D, Niedbala RS Oral-based diagnostics NY Acad Sci 2007; Boston Mass.

Recently, due to the combination of emerging biotechnologies and salivary diagnostics, a large number of medically valuable analytes in saliva are gradually unveiled and some of them represent biomarkers for different diseases (cancer, viral diseases, HIV).

These developments have extended the range of saliva-based diagnostics from simple oral cavity to the whole physiological system.

The object to provide a test being painless, inexpensive, easier, and safer than approaches based on serum or urine with an impact of molecular diagnostic is met by the method of the present invention. In one embodiment the method was modified by using a drying method (lyophilization) with a subsequent dilution to drop the sensitivity down to 0.2 µM. The present method was compared with the HPLC-technique whereby comparable results were found.

The already existing results are surprising. There is a significant difference in serum and saliva between transplanted patients and healthy volunteers. Furthermore, an inflammatory response was detected in an earlier stage (up to 5 days) than with other parameters like CRP or even clinical symptoms.

BRIEF DESCRIPTION OF THE DRAWINGS

The present invention is illustrated by the Figures:

FIG. 5 is a comparison of the kynurenine levels measured in serum and in saliva both obtained from normal, healthy control persons. The average kynurenine level in saliva of healthy people was about 0.5-0.7 μM/L kynurenine whereas the concentration of kynurenine in serum was about 2.5-3.0 μM/L kynurenine. The concentration of kynurenine is therefore about 4-5 times higher than in saliva when both samples are obtained from normal control persons.

FIG. 6 shows the stability of kynurenine after taking the sample from patients. It is important that the concentration of kynurenine in the sample remains the same for at least a substantial period of time (hours). Therefore, samples were taken, stored and the concentration of kynurenine was measured in time intervals of one hour. Within the measured time interval (up to 4 hours) no substantial change of the concentration of kynurenine was observed.

FIG. 7 shows that the kynurenine determination in saliva allows a reliable indication of potential problems in patients after having received a transplant. The Figure shows as control patients without an inflammation indicating a potential rejection of the transplant. The controls showed a concentration of kynurenine in saliva of an average of about 0.5 μM/L kynurenine. The value of kynurenine in saliva of patients showing the early signs of inflammation increased dramatically to an average value of around 7 μM/L kynurenine. Surprisingly the inflammatory response was detected 5 days before any clinical symptom occurred. This allowed the treatment of such patients at an early stage whereby the rejection of the transplant could be avoided.

FIG. 8 is a schematic overview of the kynurenine pathway, the major route of tryptophan degradation in higher eukaryotes. Enzymes are indicated in italics. The neurotoxic metabolites QUIN and 3-HK are highlighted in grey and the neuroprotective metabolite KYNA in dark grey.

FIG. 9 is a comparison of Kynurenin (measured in plasma and in saliva) in 4 groups: Control n=116; patients before heart surgery n=51; patients with postoperative cerebral disorder n=8 and patients with cerebral dementia (POCD) (before therapy) n=9. There was a significant difference between control, POCD and vascular dementia (Vasc.-Dem.) ($p<0.001$). Similar results between heart-surgery and POCD and VD ($p<0.05$) found in both plasma and saliva.

Figure 1:
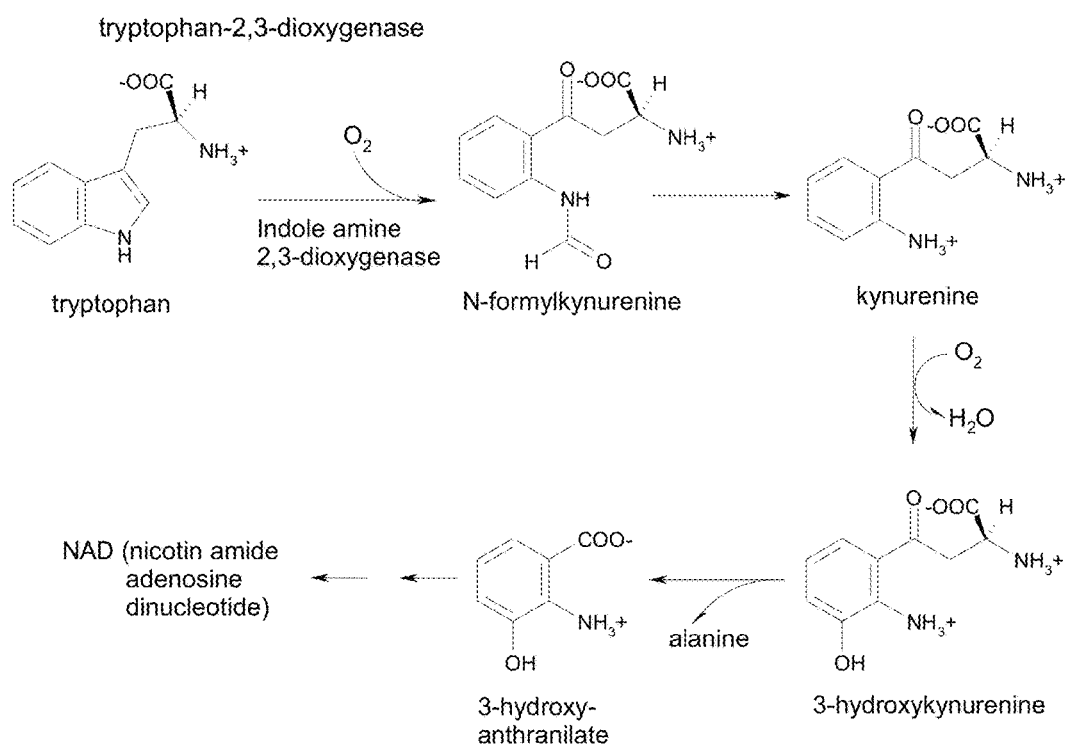
FIG. 1 shows steps of the pathway of the tryptophan degradation and thereby formed structure of kynurenine and other intermediates. The degradation of tryptophan to alanine and acetacetate is initiated by tryptophane-2,3-dioxygenase.
Figure 2:
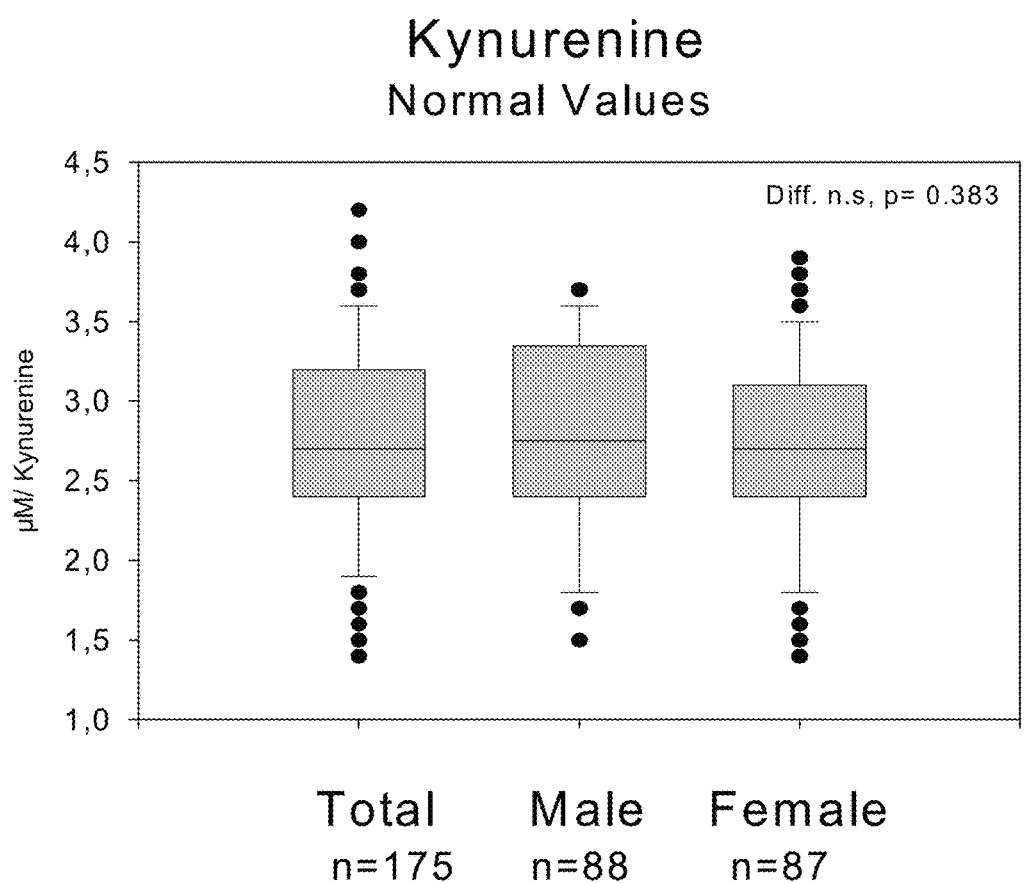
FIG. 2 is an evaluation of normal kynurenine values in the serum of healthy control. No difference between the genders has been observed. The average value of kynurenine in sera of healthy persons is between 2.5 and 3.0 μM kynurenine.
Figure 3:
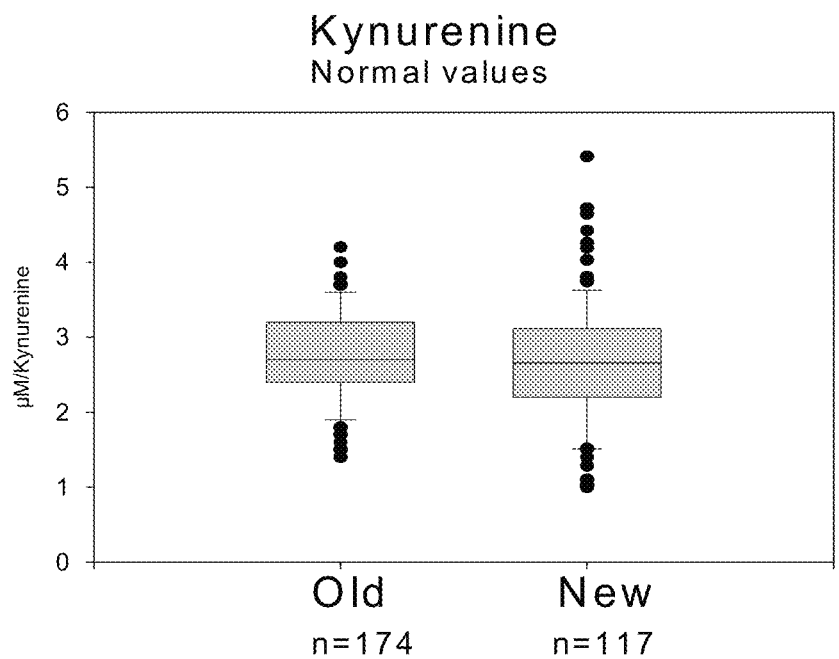
FIG. 3 is a comparison of two independent cohorts of normal healthy controls of blood donors. In the first cohort (old) 174 sera have been tested and in the second cohort (new) 117 sera of blood donors were checked. Between both groups there was no statistical difference. Nearly the same value has been measured.
Figure 4:
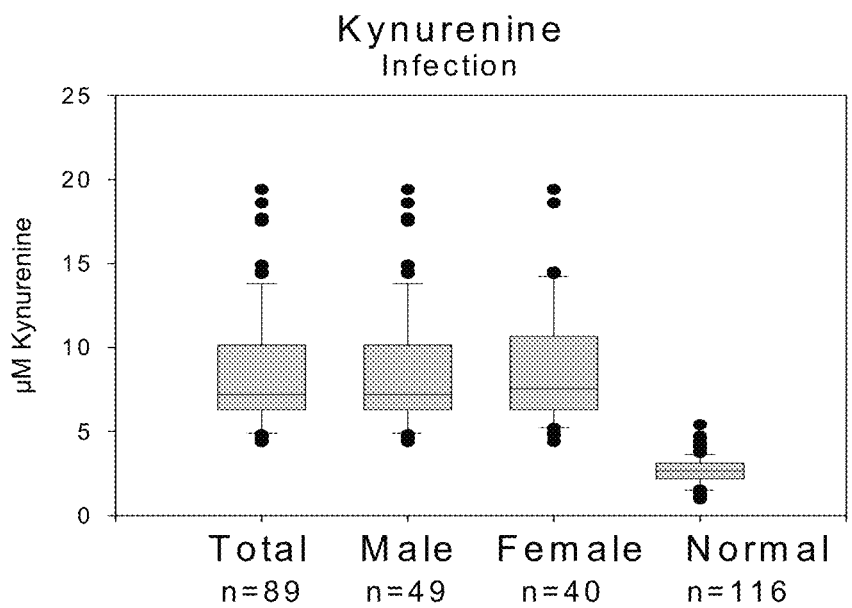
FIG. 4 shows the kynurenine concentrations in sera from non-transplanted patients who suffered under an infection such as e.g. UTI (urinary tract infection), bronchiopneumonia or greater wound infections. There was no gender difference and a significant difference to stable transplanted patients. The kynurenine values were substantially higher than the values measured in sera of normal patients. The average value ranged between about 7 to 9 μM kynurenine.

The present invention is further illustrated by the following examples which are, however, not limiting the scope of the present invention.

EXAMPLE 1

Kynurenine-Test for the diagnosis of inflammation especially of rejection episodes in transplantation 1.1. General Used Technique of Colorimetric Assay The tryptophan metabolites via kynurenine can be quantitatively determined in biologic fluids by color reactions which are known since many decades (e.g. Coppini et al., Clinical Chemistry, Vol. 5, No. 5, 1959, p. 391-401). In general a detection method via the formation of a colored reaction product can be performed by standard methods.

Microplate Readers are laboratory instruments designed to detect biological, chemical or physical events of samples in microtiter plates. They are widely used in research, drug discovery, bioassay validation, quality control as well as manufacturing processes in the pharmaceutical and biotechnological industry and academic organizations. Sample reactions can be assayed in 6-1536 well format microtiter plates. The most common microplate format used in academic research laboratories or clinical diagnostic laboratories is a 96-well (8 by 12 matrix) with a typical reaction volume between 100 and 200 μL per well. Higher density microplates (384- or 1536-well microplates) are typically used for screening applications, when throughput (number of samples/day processed) and assay cost/sample become critical parameters, with a typical assay volume between 5 and 50 μL per well.

Common detection modes for microplate assays are absorbance, fluorescence intensity, luminescence, time-resolved fluorescence, and fluorescence polarization.

Absorbance detection has been available in microplate readers for more than 3 decades, and is used for assays such as ELISA assays, protein and nucleic acid quantification or enzyme activity assays. A light source illuminates the sample using a specific wavelength (selected by an optical filter, or a monochromator), and a light detector located on the other side of the well measures how much of the initial (100%) light is transmitted through the sample: the amount of transmitted light will typically be related to the concentration of the molecule of interest.

1.2. Description of the Test

This test was developed as a modified method.

A color reagent was prepared and a dilution of a standard solution of kynurenine was also prepared. The color reaction is performed with a so-called "Ehrlich-Reagenz" which results in a yellow color. A solution comprising 2% by weight dimethylaminobenzaldehyde dissolved in 20% HCl is designated as "Ehrlich-Reagenz". Said coloring reagent serves for the detection of primary amino groups, pyrrole and indole derivatives as well. The colorimetric determination of the concentration is performed with monochromatic light. The standard solution of kynurenine was prepared by using L-kynurenine sulfate.

Equal amounts of sample were mixed with 100 μl trichloroacetic acid (30%) thoroughly. After centrifugation the supernatant was measured. The absorbents of each sample at 492 nm were compared with the absorbents at 650 nm or 690 nm of the same sample. Then the absorbents of the controls (average of 5 wells) were subtracted from the absorbents of each well. By preparing a standard curve the concentration of kynurenine in each sample could be determined.

EXAMPLE 2

Serum values were determined as follows:
In a pilot study the L-kynurenine levels were determined in >15,000 sera from >400 recipients of a renal allograft with well defined postoperative courses. The level of kynurenine reflects the degree of IDO activation. All recipients showed pre renal transplant significant elevated kynurenine levels (16.5±5 nmol/ml; healthy transplanted stable people: 5.3±1.2; organ donors: 6.5±5.5 and normal controls: 2.4±0.3; inter group differences p<0.001). The kynurenine values were determined with sera. In recipients with immediately functioning renal grafts the kynurenine levels returned to normal within 3-5 days. Every delayed graft function was associated with elevated kynurenine levels, which also returned to normal after the beginning of graft function (there is an activation during dialysis and lower excretion through urine). In recipients with primarily functionless grafts the preoperative elevated kynurenine levels did not change. In recipients with primarily functioning grafts a breakdown of graft function was promptly associated with a significant elevation of kynurenine levels. These findings give evidence for the importance of kynurenine activity also in clinical renal transplantation. An extended study enrolling 248 recipients has shown the clinical relevance of kynurenine activity as a predictive parameter for rejection as well as for long-term function.

EXAMPLE 3

Eight patients with postoperative cerebral disorders after heart surgery (valve replacement, mean age 62±6.3 years) who met the criteria (26) and nine patients with cerebral dementia (mean age 73±8.3 years, mean MMS-score 22) were enrolled in the comparative study with normal controls (n=116; mean age 48.8 years, range 12-88 y.) and patients before heart surgery (n=51, mean age 51.3, range 42-69 y.). The aim was to detect the inflammatory response after this major surgical procedure by estimating either kynurenine in plasma or in saliva. Kynurenine was significant higher in patients with POCD at day 5 postoperative. Patients with cerebral dementia showed prior start of medical treatment an elevated kynurenine level in plasma as well as in saliva.

In total, already in this very small group of patients it could be demonstrated, that kynurenine measurement is a tool to identify cerebral disorders as well as to monitor them.

The invention claimed is:
1. A method for the early detection of a potential inflammation in a patient caused by a rejection of a transplant before any clinical symptoms occur, comprising:
   obtaining a saliva sample from the patient after receiving a transplant but prior to the patient recognizing any clinical symptoms of a transplant rejection;
   measuring the level of one or more kynurenine metabolites selected from the group consisting of L-kynurenine, kynurenic acid, 3-hydroxy-L-kynurenine and combinations thereof in the saliva sample by a competitive assay utilizing kynurenine-specific antibodies;
   diagnosing the patient with a transplant rejection when said kynurenine level in the saliva sample of the patient is from about 2 μM/L to about 7 μM/L; and
   administering immunosuppressive graft-saving therapy to the diagnosed patient.

2. The method of claim 1 wherein the potential inflammation is caused by the rejection of a transplant organ selected from the group comprising liver, pancreas, heart, lung and kidney.

3. The method of claim 1 wherein the potential inflammation is caused by a transplant selected from the group comprising cornea-transplants, retina-transplants, cartilage-transplants and skin-transplants.

4. The method of claim 1 wherein the potential inflammation is caused by the rejection of an artificial transplant.

5. The method of claim 4 wherein the artificial transplant is selected from the group comprising bone replacements, joint replacements, tooth implants, cartilage implants, breast implants and penis implants.

6. A method for the early detection of a potential inflammation in a patient caused by a rejection of a transplant before any clinical symptoms occur, comprising:
   obtaining a saliva sample from the patient after receiving a transplant but prior to the patient recognizing any clinical symptoms of a transplant rejection;
   removing components from said saliva sample which may disturb the correct test result wherein said components comprise N-formyl kynurenine;
   measuring the level of one or more kynurenine metabolites selected from the group consisting of L-kynurenine, kynurenic acid, 3-hydroxy-L-kynurenine and combinations thereof in said saliva sample by a competitive assay utilizing kynurenine-specific antibodies;
   diagnosing the patient with a transplant rejection when said kynurenine level in the saliva sample of the patient is from about 2 μM/L to about 7 μM/L; and
   administering immunosuppressive graft-saving therapy to the diagnosed patient.

7. The method of claim 6, wherein the disturbing components of the saliva sample are removed by precipitation followed by centrifugation.

8. The method of claim 6, wherein the disturbing components of the saliva sample are removed by deproteinization followed by centrifugation.

9. The method of claim 1, wherein the method is utilized for monitoring the recovery of a patient after having received a transplant.

10. The method of claim 1, wherein the method is utilized for controlling therapy in a patient after having received a transplant.

* * * * *